United States Patent
Lee et al.

(10) Patent No.: US 9,911,224 B2
(45) Date of Patent: Mar. 6, 2018

(54) VOLUME RENDERING APPARATUS AND METHOD USING VOXEL BRIGHTNESS GAIN VALUES AND VOXEL SELECTING MODEL

(71) Applicant: SAMSUNG MEDISON CO., LTD., Gangwon-do (KR)

(72) Inventors: Bong-heon Lee, Gangwon-do (KR); Jin-yong Lee, Gangwon-do (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 0 days.

(21) Appl. No.: 14/689,446

(22) Filed: Apr. 17, 2015

(65) Prior Publication Data
US 2016/0155259 A1   Jun. 2, 2016

(30) Foreign Application Priority Data
Nov. 28, 2014   (KR) .................. 10-2014-0169171

(51) Int. Cl.
*G06T 15/08* (2011.01)
*A61B 8/08* (2006.01)

(52) U.S. Cl.
CPC .............. *G06T 15/08* (2013.01); *A61B 8/483* (2013.01); *A61B 8/0883* (2013.01); *A61B 8/5207* (2013.01)

(58) Field of Classification Search
CPC ...................................................... G06T 15/08
See application file for complete search history.

(56) References Cited

U.S. PATENT DOCUMENTS

| | | | |
|---|---|---|---|
| 2002/0172409 A1* | 11/2002 | Saito | G06T 15/08 382/132 |
| 2004/0125103 A1* | 7/2004 | Kaufman | G06T 15/005 345/419 |
| 2005/0136006 A1* | 6/2005 | Libutti | A61K 49/0008 424/9.2 |
| 2006/0056680 A1* | 3/2006 | Stutsman | G06T 15/08 382/154 |
| 2007/0265530 A1 | 11/2007 | Hashimoto et al. | |
| 2009/0076387 A1 | 3/2009 | Simopoulos | |
| 2010/0179428 A1* | 7/2010 | Pedersen | A61B 8/00 600/443 |
| 2011/0087095 A1 | 4/2011 | Lee | |
| 2012/0087564 A1* | 4/2012 | Tsujita | A61B 8/0808 382/131 |

(Continued)

FOREIGN PATENT DOCUMENTS

JP   8-161520 A   6/1996
JP   2002-336242 A   11/2002
(Continued)

OTHER PUBLICATIONS

Communication dated Apr. 28, 2016 issued by European Patent Office in counterpart European Application No. 15166222.8.

*Primary Examiner* — Daniel Hajnik
(74) *Attorney, Agent, or Firm* — Sughrue Mion, PLLC

(57) ABSTRACT

Provided is a volume rendering method including: obtaining 3-dimensional (3D) volume data of an object; setting a parameter of a first voxel included in the 3D volume data as a first value, and a parameter of a second voxel included in the 3D volume data as a second value; and performing rendering by applying the first value to the first voxel and the second value to the second voxel.

13 Claims, 18 Drawing Sheets

(56) References Cited

U.S. PATENT DOCUMENTS

| | | | |
|---|---|---|---|
| 2013/0004047 A1 | 1/2013 | Shiki et al. | |
| 2013/0021341 A1* | 1/2013 | Choi | G06T 19/00 345/424 |
| 2013/0051645 A1* | 2/2013 | Kim | G06K 9/00 382/131 |
| 2013/0156280 A1* | 6/2013 | Kadir | G06T 7/0012 382/128 |
| 2013/0198687 A1* | 8/2013 | Bird | A61B 5/7425 715/810 |
| 2013/0303913 A1* | 11/2013 | Tian | A61B 8/483 600/447 |
| 2014/0003691 A1* | 1/2014 | Serlie | G06T 11/003 382/131 |
| 2014/0088428 A1 | 3/2014 | Yang et al. | |
| 2014/0176596 A1* | 6/2014 | Kodavalla | G06T 11/001 345/604 |
| 2015/0078641 A1* | 3/2015 | Tan | G06T 7/0083 382/131 |

FOREIGN PATENT DOCUMENTS

| | | |
|---|---|---|
| KR | 10-1100457 B1 | 12/2011 |
| KR | 10-2014-0048449 A | 4/2014 |

\* cited by examiner

FIG. 16A
FIG. 16B
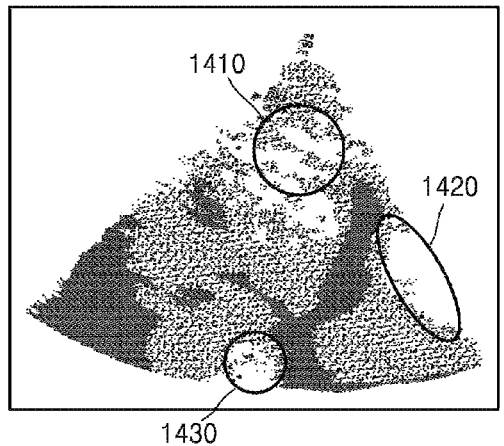
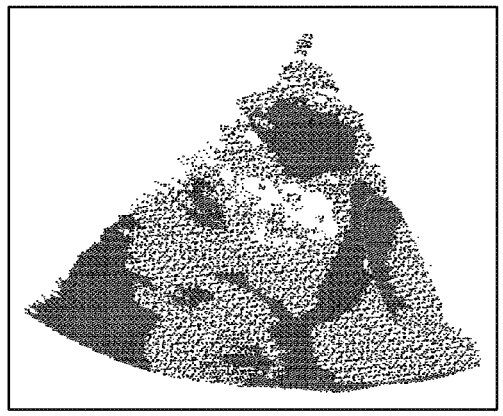

VOLUME RENDERING APPARATUS AND METHOD USING VOXEL BRIGHTNESS GAIN VALUES AND VOXEL SELECTING MODEL

RELATED APPLICATION

This application claims the benefit of Korean Patent Application No. 10-2014-0169171, filed on Nov. 28, 2014, in the Korean Intellectual Property Office, the disclosure of which is incorporated herein in its entirety by reference.

BACKGROUND

1. Field

One or more exemplary embodiments relate to a volume rendering apparatus and a volume rendering method, and more particularly, to a volume rendering apparatus and a volume rendering method, which perform volume rendering by locally applying a gain value or a threshold value.

2. Description of the Related Art

Recently, in various medical fields, medical imaging apparatuses for imaging and obtaining information about biological tissues of a human body have become widely used to diagnose early or treat various diseases. Examples of such medical imaging apparatuses include an ultrasound diagnosis apparatus, a computerized tomography (CT) apparatus, and a magnetic resonance imaging (MRI) apparatus.

Ultrasound diagnosis apparatuses transmit ultrasound signals generated by transducers of a probe to an object and receive echo signals reflected from the object, thereby obtaining at least one image of an internal part of the object. In particular, ultrasound diagnosis apparatuses are used for medical purposes including observation of the interior of an object, detection of foreign substances, and diagnosis of damage to the object. Such ultrasound diagnosis apparatuses provide high stability, display images in real-time, and are safe due to the lack of radioactive exposure, compared to X-ray apparatuses.

Meanwhile, volume data indicating a volume of a 3-dimensional (3D) object, obtained by such ultrasound diagnosis apparatuses, is visualized as visual information for diagnosis. For example, in volume rendering, a 2D image is displayed by projecting the volume data on a 2D screen, and by using the volume rendering, an image in which the interior of a 3D object or 3D semitransparent materials are visualized may be displayed.

SUMMARY

One or more exemplary embodiments include a volume rendering apparatus and a volume rendering method, which perform rendering by applying a gain value or a threshold value to some voxels included in volume data of an object differently from the remaining voxels to provide a rendered image having an improved quality overall.

Additional aspects will be set forth in part in the description which follows and, in part, will be apparent from the description, or may be learned by practice of the presented embodiments.

According to one or more exemplary embodiments, a volume rendering method includes: obtaining 3-dimensional (3D) volume data of an object; setting a parameter of a first voxel included in the 3D volume data as a first value, and a parameter of a second voxel included in the 3D volume data as a second value; and performing rendering by applying the first value to the first voxel and the second value to the second voxel.

Each parameter may include at least one of a gain value and a threshold value applied to voxels included in the 3D volume data while performing the rendering, and the first value may include at least one of a first gain value and a first threshold value, and the second value comprises at least one of a second gain value and a second threshold value.

The performing of the rendering may include amplifying or attenuating a brightness value of the first voxel based on the first gain value, and amplifying or attenuating a brightness value of the second voxel based on the second gain value.

The performing of the rendering may include setting the brightness value of the first voxel to 0 when the brightness value of the first voxel is lower than the first threshold value, and setting the brightness value of the second voxel to 0 when the brightness value of the second voxel is lower than the second threshold value.

The first voxel and the second voxel may be voxels located at a same distance from a viewpoint of the rendering.

The volume rendering method may further include receiving a user input of selecting at least one of the first voxel and the second voxel.

The volume rendering method may further include: receiving a user input of selecting a pre-stored voxel selecting model; and setting at least one of the first voxel and the second voxel based on the pre-stored voxel selecting model.

The pre-stored voxel selecting model may be a model pre-set based on a type of the object.

The volume rendering method may further include receiving a user input of setting at least one of the first value and the second value.

The first value may be determined based on a type of the object and a location of the first voxel, and the second value may be determined based on the type of the object and a location of the second voxel.

The volume data may be ultrasound volume data.

According to one or more exemplary embodiments, a volume rendering apparatus includes: a data obtainer that obtains 3-dimensional (3D) volume data of an object; a parameter setter that sets a parameter of a first voxel included in the 3D volume data as a first value, and a parameter of a second voxel included in the 3D volume data as a second value; and a renderer that performs rendering by applying the first value to the first voxel and the second value to the second voxel.

Each parameter may include at least one of a gain value and a threshold value applied to voxels included in the 3D volume data while performing the rendering, and the first value may include at least one of a first gain value and a first threshold value, and the second value may include at least one of a second gain value and a second threshold value.

The renderer may amplify or attenuate a brightness value of the first voxel based on the first gain value, and amplify or attenuate a brightness value of the second voxel based on the second gain value.

The renderer may set the brightness value of the first voxel to 0 when the brightness value of the first voxel is lower than the first threshold value, and set the brightness value of the second voxel to 0 when the brightness value of the second voxel is lower than the second threshold value.

The first voxel and the second voxel may be voxels located at a same distance from a viewpoint of the rendering.

The volume rendering apparatus may further include a user input unit that receives a user input of selecting at least one of the first voxel and the second voxel.

The user input unit may receive a user input of selecting a pre-stored voxel selecting model, and the parameter setter may set at least one of the first voxel and the second voxel based on the pre-stored voxel selecting model.

The pre-stored voxel selecting model may be a model pre-set based on a type of the object.

The volume rendering apparatus may further include a user input unit that receives a user input of setting at least one of the first value and the second value.

The first value may be determined based on a type of the object and a location of the first voxel, and the second value may be determined based on the type of the object and a location of the second voxel.

BRIEF DESCRIPTION OF THE DRAWINGS

Embodiments of the invention now will be described more fully hereinafter with reference to the accompanying drawings, in which reference numerals denote structural elements.

FIGS. 16A and 16B are diagrams of volume rendered images according to exemplary embodiments;

DETAILED DESCRIPTION

Figure 1:
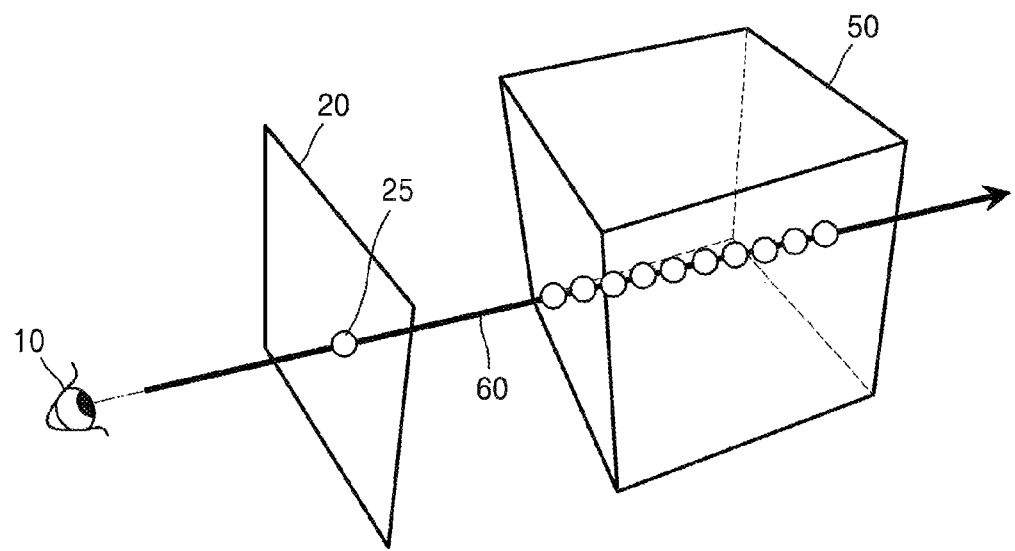
FIG. 1 is a diagram for describing a volume rendering method, according to an exemplary embodiment.

Hereinafter, the terms used in the specification will be briefly described, and then one or more exemplary embodiments will be described in detail.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element and may further include another element. In addition, terms such as ". . . unit", ". . . module", or the like refer to units that perform at least one function or operation, and the units may be implemented as hardware or software or as a combination of hardware and software.

Throughout the specification, an "image" may mean multi-dimensional data formed of discrete image elements, e.g., pixels in a two-dimensional (2D) image and voxels in a three-dimensional (3D) image. Examples of the image include medical images (ultrasound images, computerized tomography (CT) images, and magnetic resonance (MR) images) of objects obtained by using ultrasound apparatuses, CT apparatuses, and magnetic resonance imaging (MRI) apparatuses, but are not limited thereto.

An "ultrasound image" may mean an image obtained by transmitting an ultrasound signal generated by a transducer of a probe to an object, and receiving information of an echo signal reflected from the object. Here, the ultrasound image may vary, for example, may be in any one of an amplitude (A) mode, a brightness (B) mode, a color (C) mode, or a Doppler (D) mode.

A "CT image" may mean an image generated by synthesizing a plurality of X-ray images that are obtained by photographing an object while a CT imaging apparatus rotates around at least one axis with respect to the object.

An "MR image" may mean an image of an object obtained by using nuclear magnetic resonance principles.

Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

FIG. 1 is a diagram for describing a volume rendering method, according to an exemplary embodiment.

Volume rendering of a 3D medical image may be performed based on a model including a viewpoint, a line of sight, a screen, and volume data.

As shown in FIG. 1, during the volume rendering of the 3D medical image, a volume rendering apparatus may determine a viewpoint 10 and a screen 20 according to the viewpoint 10. Here, the viewpoint 10 is a direction of a viewer observing volume data 50. Also, the screen 20 is a projected plane on which the volume data 50 is projected from the viewpoint 10, and is a 2D screen on which an image generated as the volume rendering apparatus performs the volume rendering is displayed.

The volume data 50 may indicate data reconstructed in 3D as cross-sectional images of human tissues photographed by using a medical imaging apparatus, such as an ultrasound diagnosis apparatus, a CT apparatus, or an MRI apparatus, are accumulated. The volume data 50 may include a plurality of voxels. Here, a voxel is a compound word of volume and a pixel. A pixel defines a point on a plane, whereas a voxel defines a point in 3D space. Also, the pixel includes X- and Y-coordinates, where as the voxel includes X-, Y-, and Z-coordinates.

In FIG. 1, the volume data 50 has a rectangular parallelepiped shape, but a shape of the volume data 50 is not limited thereto and may vary based on a type of a probe used by an ultrasound diagnosis apparatus.

Figure 2A:
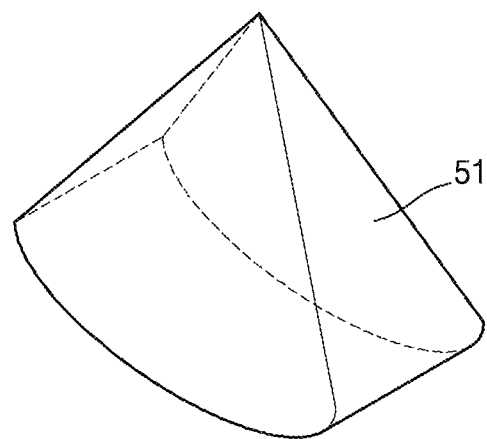
FIGS. 2A through 2C illustrate examples of volume data according to exemplary embodiments.
Figure 2B:
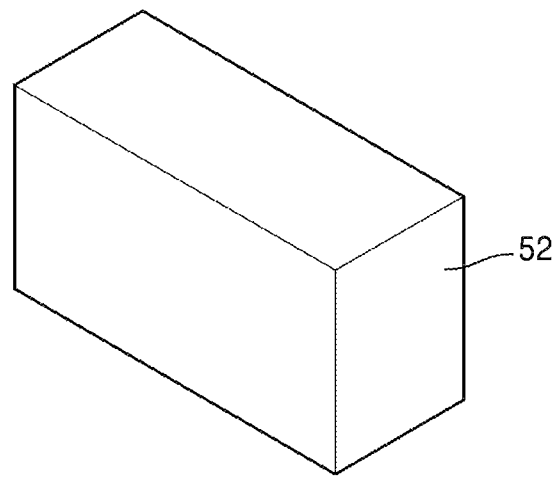
Figure 2C:
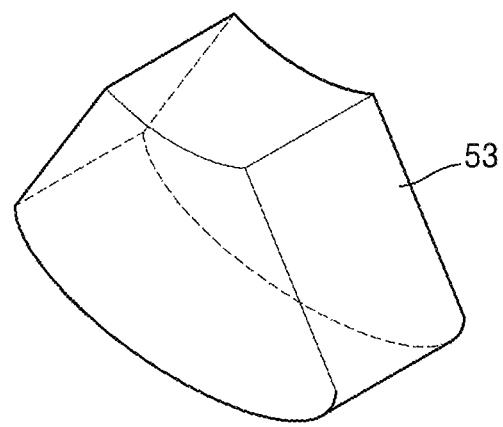

FIGS. 2A through 2C illustrate examples of the volume 50 data according to exemplary embodiments.

For example, the volume data 50 may be obtained by using a phased probe, a linear probe, or a convex probe. The volume data 50 obtained by using a phased probe may have a first shape 51 as shown in FIG. 2A. Also, the volume data 50 obtained by using a linear probe may have a second shape 52 as shown in FIG. 2B, and the volume data 50 obtained by using a convex probe may have a third shape 53 as shown in FIG. 2C. Hereinafter, for convenience of description, it is assumed that the volume data 50 has the first shape 51, but the shape of the volume data 50 is not limited thereto, and may vary.

Referring back to FIG. 1, the volume rendering apparatus according to an exemplary embodiment may perform the volume rendering by using a ray casting method. For example, as shown in FIG. 1, the ray casting method emits a virtual ray 60 towards a certain pixel 25 on a display screen from the viewpoint 10, and detects voxels through which the virtual ray 60 penetrates from among the voxels of the volume data 50. Also, the volume rendering apparatus may determine a brightness value (or transparency) of the certain pixel 25 based on brightness values of the detected voxels.

For example, the volume rendering apparatus may determine a highest brightness value of the brightness values of the detected voxels as the brightness value of the certain pixel 25. Alternatively, the volume rendering apparatus may determine a lowest brightness value of the brightness values of the detected voxels as the brightness value of the certain pixel 25. Alternatively, the volume rendering apparatus may determine an average value of the brightness values of the detected voxels as the brightness value of the certain pixel 25. However, an exemplary embodiment is not limited thereto.

The volume rendering apparatus may perform the volume rendering on the volume data 50 by using any one of various well-known volume rendering methods, as well as the volume rendering method described above.

Figure 3:
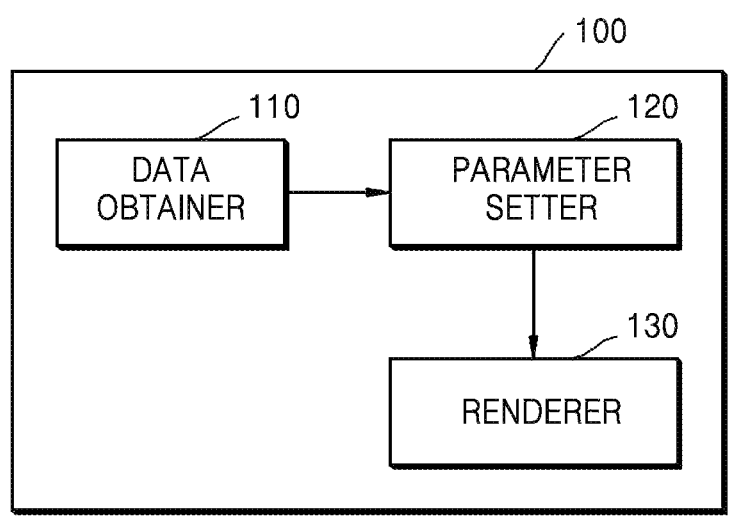
FIG. 3 is a block diagram of a volume rendering apparatus according to an exemplary embodiment.

FIG. 3 is a block diagram of a volume rendering apparatus 100 according to an exemplary embodiment.

Referring to FIG. 3, the volume rendering apparatus 100 may include a data obtainer 110, a parameter setter 120, and a renderer 130.

The data obtainer 110 may obtain volume data of an object. For example, the data obtainer 110 may transmit an ultrasound signal to the object and receive an echo signal reflected from the object. The data obtainer 110 may process the received echo signal to generate 3D ultrasound volume data of the object.

Alternatively, the data obtainer 110 may transmit a radio frequency (RF) signal to the object and receive an MR signal emitted from the object. The data obtainer 110 may process the received MR signal to generate 3D MR volume data of the object.

Alternatively, the data obtainer 110 may transmit X-ray to the object and detect an X-ray signal transmitted through the object. The data obtainer 110 may process the detected X-ray signal to generate 3D CT volume data of the object.

Alternatively, the data obtainer 110 may not directly generate volume data upon receiving an ultrasound signal, an MR signal, or an X-ray signal from the object, but may receive volume data generated by an external apparatus, such as an ultrasound diagnosis apparatus, an MR apparatus, or a CT apparatus.

The parameter setter 120 may set a parameter of a first voxel from among voxels included in the volume data as a first value, and a parameter of a second voxel as a second value. Here, a parameter may include a gain value or a threshold value applied to a voxel during volume rendering.

For example, the parameter setter 120 may set a first gain value or a first threshold value regarding the first voxel, and set a second gain value or a second threshold value regarding the second voxel. Here, at least one of the first gain value, the first threshold value, the second gain value, and the second threshold value may be a value set according to a user input. Alternatively, the first gain value or the first threshold value may be set based on at least one of a type of the object and a location of the first voxel, and the second gain value or the second threshold value may be set based on at least one of the type of the object and a location of the second voxel.

The renderer 130 may apply the first gain value or the first threshold value to the first voxel, and the second gain value or the second threshold value to the second voxel. For example, the renderer 130 may amplify or attenuate a brightness value of the first voxel based on the first gain value, and amplify or attenuate a brightness value of the second voxel based on the second gain value. Alternatively, the renderer 130 may set the brightness value of the first voxel to 0 when the brightness value of the first voxel is lower than the first threshold value, and set the brightness value of the second voxel to 0 when the brightness value of the second voxel is lower than the second threshold value.

The renderer 130 may perform the volume rendering based on the first voxel or the second voxel to which the first gain or threshold value or the second gain or threshold value is applied.

Figure 4:
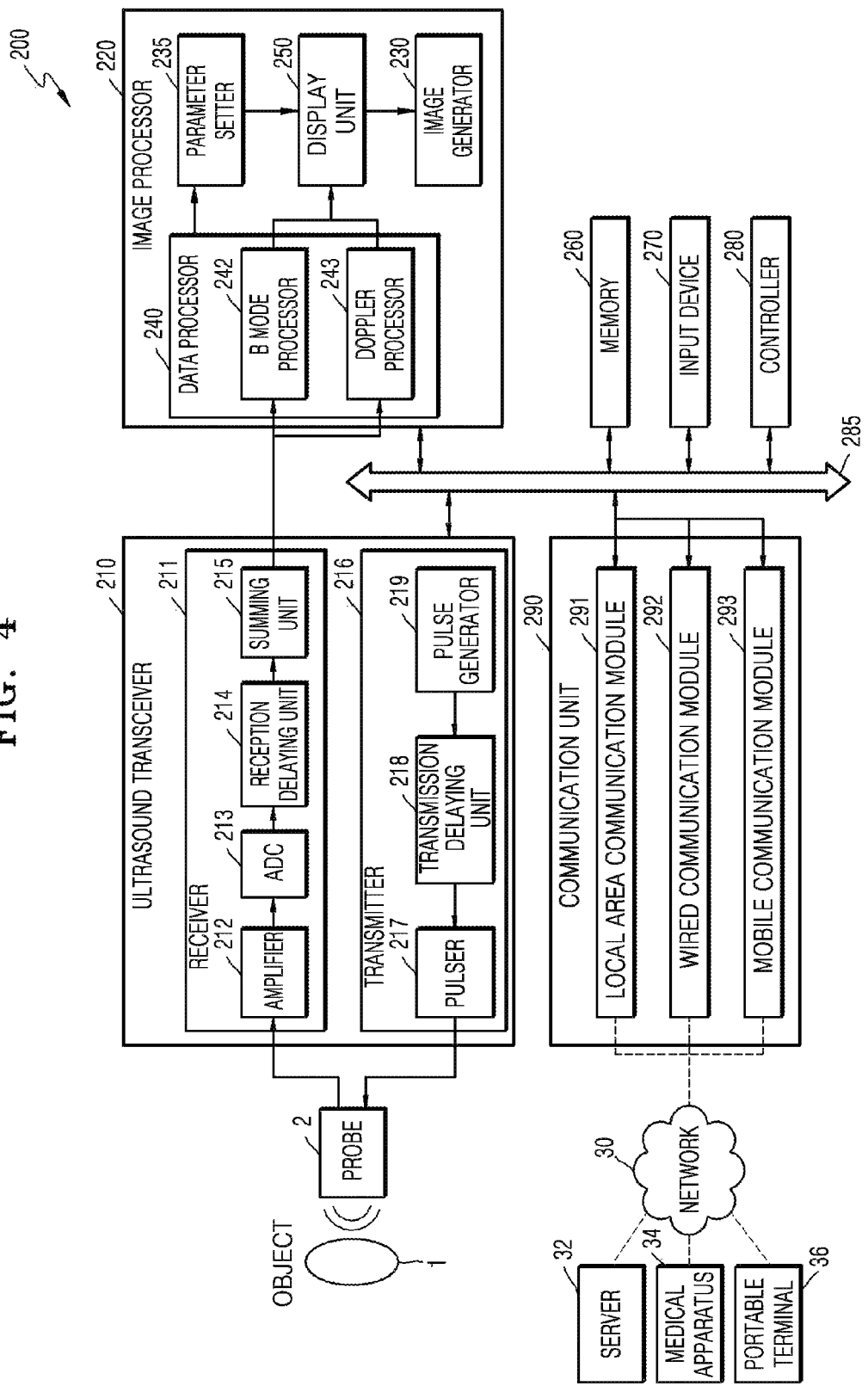
FIG. 4 is a block diagram of a volume rendering apparatus according to another exemplary embodiment.

FIG. 4 is a block diagram of a volume rendering apparatus 200 according to another exemplary embodiment.

Referring to FIG. 4, the volume rendering apparatus 200 according to an exemplary embodiment may be an ultrasound diagnosis apparatus, and may include a probe 2, an ultrasound transceiver 210, an image processor 220, a display unit 250, a communication unit 290, a memory 260, a user input unit 270, and a controller 280. The above components may be connected to each other through a bus 285, and the image processor 220 may include a parameter setter 235, an image generator 230, and the display unit 250.

The data obtainer 110 of FIG. 3 may correspond to the ultrasound transceiver 210 and a data processor 240 of FIG. 4, the parameter setter 120 of FIG. 3 may correspond to the parameter setter 235 of FIG. 4, and the renderer 130 of FIG. 3 may correspond to the image generator 230 of FIG. 4. Accordingly, descriptions about the data obtainer 11, the parameter setter 120, and the renderer 130 may also be applied to the ultrasound transceiver 210, the data processor 240, the parameter setter 235, and the image generator 230, and thus details thereof are not provided again.

The volume rendering apparatus 200 according to an exemplary embodiment may be a cart type apparatus or a portable type apparatus. Examples of the portable type apparatus may include, but are not limited to, a picture archiving and communication system (PACS) viewer, a smartphone, a laptop computer, a personal digital assistant (PDA), and a tablet PC.

The probe 2 transmits an ultrasound signal to an object 1 in response to a driving signal applied by the ultrasound transceiver 210 and receives an echo signal reflected by the object 1. The probe 2 includes a plurality of transducers, and the plurality of transducers oscillate in response to electric signals and generate acoustic energy, that is, ultrasound waves. Furthermore, the probe 2 may be connected to a main body of the volume rendering apparatus 200 by wire or wirelessly.

A transmitter 216 supplies a driving signal to the probe 2. The transmitter 216 includes a pulse generator 219, a transmission delaying unit 218, and a pulser 217. The pulse generator 219 generates pulses for forming transmission ultrasound waves based on a certain pulse repetition frequency (PRF), and the transmission delaying unit 218 delays the pulses by delay times necessary for determining transmission directionality. The pulses which have been delayed correspond to a plurality of piezoelectric vibrators included in the probe 2, respectively. The pulser 217 applies a driving signal (or a driving pulse) to the probe 2 based on timing corresponding to each of the pulses which have been delayed.

A receiver 211 generates ultrasound data by processing echo signals received from the probe 2. The receiver 211 may include an amplifier 212, an analog-to-digital converter (ADC) 213, a reception delaying unit 214, and a summing unit 215. The amplifier 212 amplifies echo signals in each channel, and the ADC 213 performs analog-to-digital conversion with respect to the amplified echo signals. The reception delaying unit 214 delays digital echo signals output by the ADC 1124 by delay times necessary for determining reception directionality, and the summing unit 215 generates ultrasound data by summing the echo signals processed by the reception delaying unit 214. In some embodiments, the receiver 211 may not include the amplifier 212. In other words, if the sensitivity of the probe 2 or the capability of the ADC 213 to process bits is enhanced, the amplifier 212 may be omitted.

The image processor 220 generates an ultrasound image by scan-converting ultrasound data generated by the ultrasound transceiver 210 and displays the ultrasound image. The ultrasound image may be not only a grayscale ultrasound image obtained by scanning the object 1 in an amplitude (A) mode, a brightness (B) mode, and a motion (M) mode, but also a Doppler image showing a movement of the object 1 via a Doppler effect. The Doppler image may be a blood flow Doppler image showing flow of blood (also referred to as a color Doppler image), a tissue Doppler image showing a movement of tissue, or a spectral Doppler image showing a moving speed of the object 1 as a waveform.

A B mode processor 242 extracts B mode components from ultrasound data and processes the B mode components. The image generator 230 may generate an ultrasound image indicating signal intensities as brightness based on the B mode components extracted by the B mode processor 242.

Similarly, a Doppler processor 243 may extract Doppler components from ultrasound data, and the image generator 230 may generate a Doppler image indicating a movement of the object 1 as colors or waveforms based on the extracted Doppler components.

According to an exemplary embodiment, the image generator 230 may generate 2D ultrasound image or a 3D image of the object 1, and may also generate an elasticity image by imaging deformation of the object 1 due to pressure. Furthermore, the image generator 230 may display various pieces of additional information in an ultrasound image by using text and graphics. In addition, the generated ultrasound image may be stored in the memory 260.

The display 250 displays the generated ultrasound image. The display 250 may display not only an ultrasound image, but also various pieces of information processed by the volume rendering apparatus 200 on a screen image via a graphical user interface (GUI).

For example, the display unit 250 may display a voxel selecting model for selecting some of voxels of volume data. The voxel selecting model may be a mode pre-set based on a shape of volume data and a type of the object 1, or arbitrarily pre-set by a user. Alternatively, the display unit 250 may display a user interface for setting a gain value or a threshold value of a first or second voxel.

In addition, the volume rendering apparatus 200 may include two or more display units 250 according to embodiments. The display unit 250 may include at least one of a liquid crystal display, a thin-film transistor-liquid crystal display, an organic light-emitting diode, a flexible display, a 3D display, and an electrophoretic display.

Also, when the display unit 250 and a user input unit (the user input unit 270) are combined in a layer structure to form a touch screen, the display unit 250 may also be used as an input device capable of receiving information according to a touch of a user, as well as an output device.

The touch screen may be configured to detect not only a touched location and a touched area but also a touched pressure. Also, the touch screen may be configured to detect not only a real-touch but also a proximity touch.

Herein, a 'real-touch' indicates a case where a pointer actually touches a screen, and a 'proximity-touch' indicates a case where a pointer does not actually touch a screen but approaches the screen while still maintaining a predetermined distance therefrom. Herein, a pointer is a touching tool for touching or proximity-touching a certain portion of a displayed screen. Examples of the pointer include an electronic pen or a finger.

Although not shown, the volume rendering apparatus 200 may include various sensors inside or near a touch screen to detect a real-touch or a proximity touch on the touch screen. An example of a sensor for detecting a touch on a touch screen includes a tactile sensor.

A tactile sensor is a sensor for detecting, with sensitivity similar to that of a person, contact of a certain object. The tactile sensor may detect various types of information, for example, roughness of a contact surface, rigidness of the certain object, and a temperature of a contact point.

Another example of the sensor for detecting a touch on a touch screen includes a proximity sensor. The proximity sensor is a sensor for detecting an existence of an object approaching or near a predetermined detection surface by using force of an electromagnetic field or an infrared light, without having to detect a mechanical touch.

Examples of the proximity sensor include a transmission type photoelectric sensor, a direct reflection type photoelectric sensor, a mirror reflection type photoelectric sensor, a high frequency oscillation type proximity sensor, a capacitance type proximity sensor, a magnetic proximity sensor, and an infrared proximity sensor.

The communication unit 290 is connected to a network 30 by wire or wirelessly to communicate with an external device or a server. The communication unit 290 may exchange data with a hospital server or a medical apparatus in a hospital, which is connected thereto via a picture archiving and communication system (PACS). Furthermore, the communication unit 290 may perform data communication according to the digital imaging and communications in medicine (DICOM) standard.

The communication unit 290 may transmit or receive data related to diagnosis of the object 1, e.g., an ultrasound image, ultrasound data, and Doppler data of the object 1, via the network 30 and may also transmit or receive medical images captured by a medical apparatus, e.g., a CT apparatus, an MRI apparatus, or an X-ray apparatus. Furthermore, the communication unit 290 may receive information about a diagnosis history or medical treatment schedule of a patient from a server and utilizes the received information to diagnose the patient. Furthermore, the communication unit 290 may perform data communication not only with a server or a medical apparatus in a hospital, but also with a portable terminal of a medical doctor or patient.

The communication unit 290 is connected to the network 30 by wire or wirelessly to exchange data with a server 32, a medical apparatus 34, or a portable terminal 36. The communication unit 290 may include one or more components for communication with external devices. For example, the communication unit 290 may include a local area communication module 291, a wired communication module 292, and a mobile communication module 293.

The local area communication module 291 refers to a module for local area communication within a predetermined distance. Examples of local area communication techniques according to an exemplary embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 292 refers to a module for communication using electric signals or optical signals. Examples of wired communication techniques according to an exemplary embodiment may include communication via a pair cable, a coaxial cable, an optical fiber cable, and an Ethernet cable.

The mobile communication module 293 transmits or receives wireless signals to or from at least one selected from a base station, an external terminal, and a server on a mobile communication network. The wireless signals may be voice call signals, video call signals, or various types of data for transmission and reception of text/multimedia messages.

The memory 260 stores various types of information processed by the volume rendering apparatus 200. For example, the memory 260 may store medical data related to diagnosis of the object 1, such as ultrasound data and an ultrasound image that are input or output, and may also store algorithms or programs which are to be executed in the volume rendering apparatus 200.

The memory 260 may be any of various storage media, e.g., a flash memory, a hard disk drive, EEPROM, etc. Furthermore, the volume rendering apparatus 200 may utilize web storage or a cloud server that performs the storage function of the memory 260 online.

The user input unit 270 generates input data that is input to control operations of the volume rendering apparatus 200 by a user. For example, the user input unit 270 may receive a user input of setting one of the voxels included in the volume data as the first voxel or the second voxel. Also, the user input unit 270 may receive a user input of setting a first gain value or a first threshold value of the first voxel or a user input of setting a second gain value or a second threshold value of the second voxel.

The user input unit 270 may include a hardware component, such as a keypad, a mouse, a touch pad, a track ball, or a jog switch, but is not limited thereto, and may further include at least one of various components, such as an electrocardiogram (ECG) measuring module, a breath measuring module, a voice recognizing sensor, a gesture recognizing sensor, a fingerprint recognizing sensor, an iris recognizing sensor, a depth sensor, and a distance sensor.

In detail, the user input unit 270 may include the touch screen in which the touch pad forms a layer structure with the display unit 250.

Here, the volume rendering apparatus 200 according to an exemplary embodiment may display an ultrasound image in a certain mode and a control panel for the ultrasound image, on the touch screen. Also, the volume rendering apparatus 200 may detect a touch gesture of the user on the ultrasound image via the touch screen.

The volume rendering apparatus 200 according to an exemplary embodiment may physically include some buttons that are frequently used by the user from among buttons included in a control panel of a general ultrasound apparatus, and provide the remaining buttons through the touch screen, in forms of GUI.

The controller 280 may control all operations of the volume rendering apparatus 200. In other words, the controller 280 may control operations among the probe 2, the ultrasound transceiver 210, the image processor 220, the communication unit 290, the memory 260, and the user input unit 270 shown in FIG. 4.

All or some of the probe 2, the ultrasound transceiver 210, the image processor 220, the communication unit 290, the memory 260, the user input unit 270, and the controller 280 may be implemented as software modules. However, one or more exemplary embodiments are not limited thereto, and some of the components stated above may be implemented as hardware modules. Furthermore, at least one selected from the ultrasound transceiver 210, the image processor 220, and the communication unit 290 may be included in the controller 280. However, one or more exemplary embodiments are not limited thereto.

Figure 5:
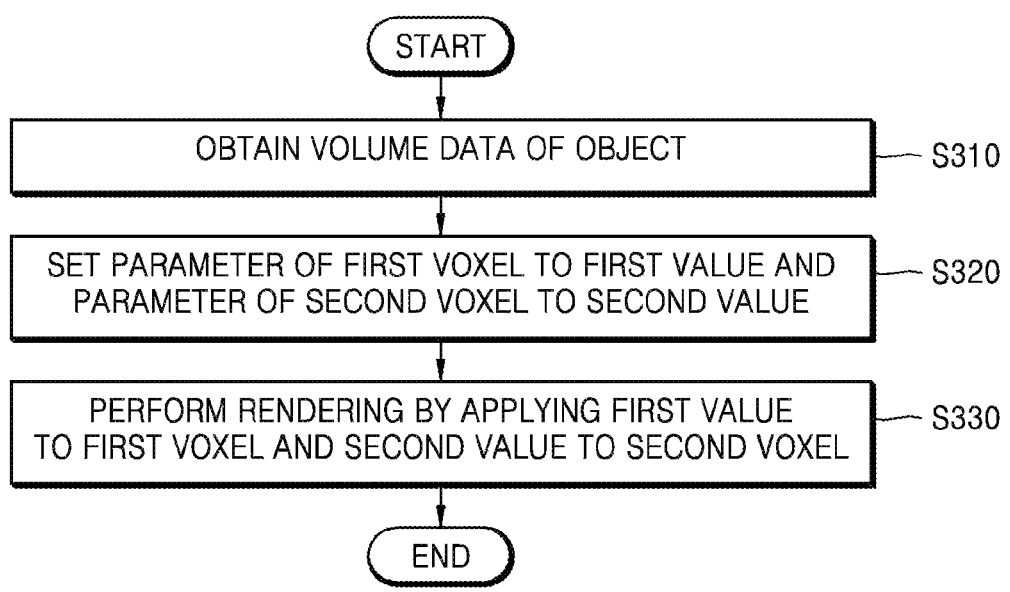
FIG. 5 is a flowchart of a volume rendering method according to an exemplary embodiment.

FIG. 5 is a flowchart of a volume rendering method according to an exemplary embodiment.

Referring to FIG. 5, the volume rendering apparatus 100 may obtain volume data of an object, in operation S310.

For example, volume data may be data reconstructed in 3D as cross-sectional images of human tissues, which are captured by using a medical imaging apparatus, such as an ultrasound diagnosis apparatus, a CT apparatus, or an MRI apparatus, are accumulated. As described above with reference to FIG. 2, the volume data may have any one of various shapes.

The volume rendering apparatus 100 may set a parameter of a first voxel from among a plurality of voxels included in the volume data to a first value, and a parameter of a second voxel to a second value, in operation S320.

The volume rendering apparatus 100 may receive a user input of selecting the first or second voxel to set the first or second voxel. For example, a user may select at least one of the plurality of voxels included in the volume data to set the first voxel, and select the remaining voxels as the second voxels. Alternatively, the user may select at least one of the plurality of voxels included in the volume data to set the first voxel, and select at least one of the remaining voxels as the second voxel.

Alternatively, the volume rendering apparatus 200 may set the first and second voxels based on a pre-set voxel selecting model, which will be described in detail later with reference to FIG. 10.

Meanwhile, a parameter according to an exemplary embodiment may include at least one of a gain value and a threshold value applied to a voxel included in volume data. Here, the gain value may be a reference value that amplifies or attenuates a brightness value of the voxel, and the threshold value may be a value indicating whether to use the brightness value of the voxel during volume rendering. For example, when the brightness value of the voxel is lower than the threshold value, the brightness value may be set to 0.

The volume rendering apparatus 100 may set a gain value of the first voxel as a first gain value or a threshold value of the first voxel as a first threshold value, and may set a gain value of the second voxel as a second gain value or a threshold value of the second voxel as a second threshold value. The volume rendering apparatus 100 may set a parameter of the first voxel or a parameter of the second voxel based on a user input. For example, the user may set the first gain value or the first threshold value of the first voxel, or set the second gain value or the second threshold value of the second voxel.

Alternatively, the volume rendering apparatus 100 may obtain the first gain value or the first threshold value of the first voxel, or obtain the second gain value or the second threshold value of the second voxel by using a pre-set function that uses a location value of a voxel as a variable.

For example, the volume rendering apparatus 100 may obtain the first gain value or the first threshold value by inputting X-, Y-, and Z-coordinate values of the first voxel to the pre-set function. Alternatively, the volume rendering apparatus 100 may obtain the second gain value or the second threshold value by inputting X-, Y-, and Z-coordinate values of the second voxel to the pre-set function.

Alternatively, the first gain value or the first threshold value, and the second gain value or the second threshold value may be pre-set values.

The volume rendering apparatus 100 may perform rendering on the volume data by applying the first value to the first voxel and the second value to the second voxel, in operation S330.

For example, the volume rendering apparatus 100 may amplify or attenuate the brightness value of the first voxel based on the first gain value, and set the brightness value of the first voxel to 0 when the brightness value of the first voxel is lower than the first threshold value. Also, the volume rendering apparatus 100 may amplify or attenuate the brightness value of the second voxel based on the second gain value, and set the brightness value of the second voxel to 0 when the brightness value of the second voxel is lower than the second threshold value.

The volume rendering apparatus 100 may perform rendering on the volume data based on the brightness value of the first voxel, to which at least one of the first gain value and the first threshold value is applied, and the brightness value of the second voxel, to which at least one of the second gain value and the second threshold value is applied, as will be described in detail later with reference to FIG. 15.

Figure 6:
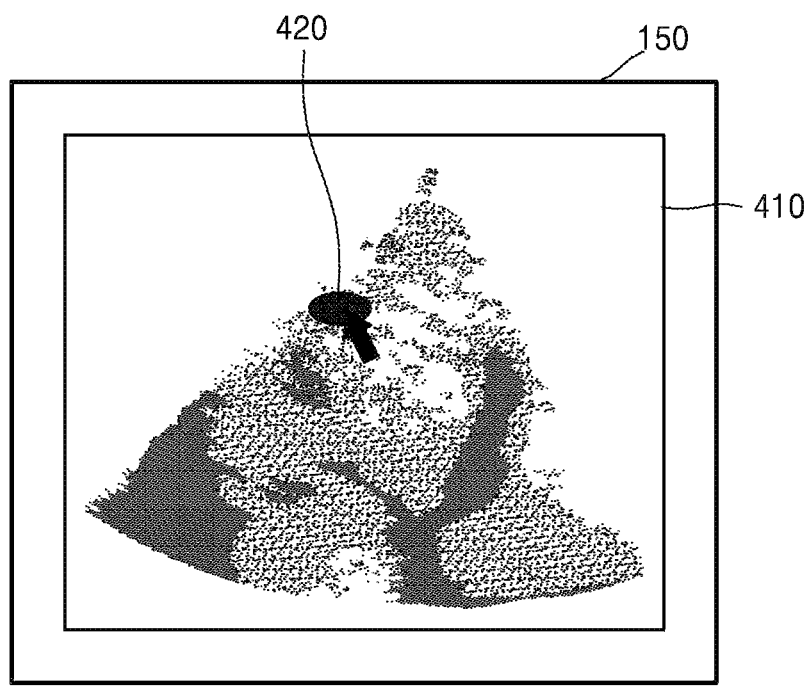
FIGS. 6 through 8 are diagrams for describing setting of a first voxel and a second voxel, according to exemplary embodiments.
Figure 7:
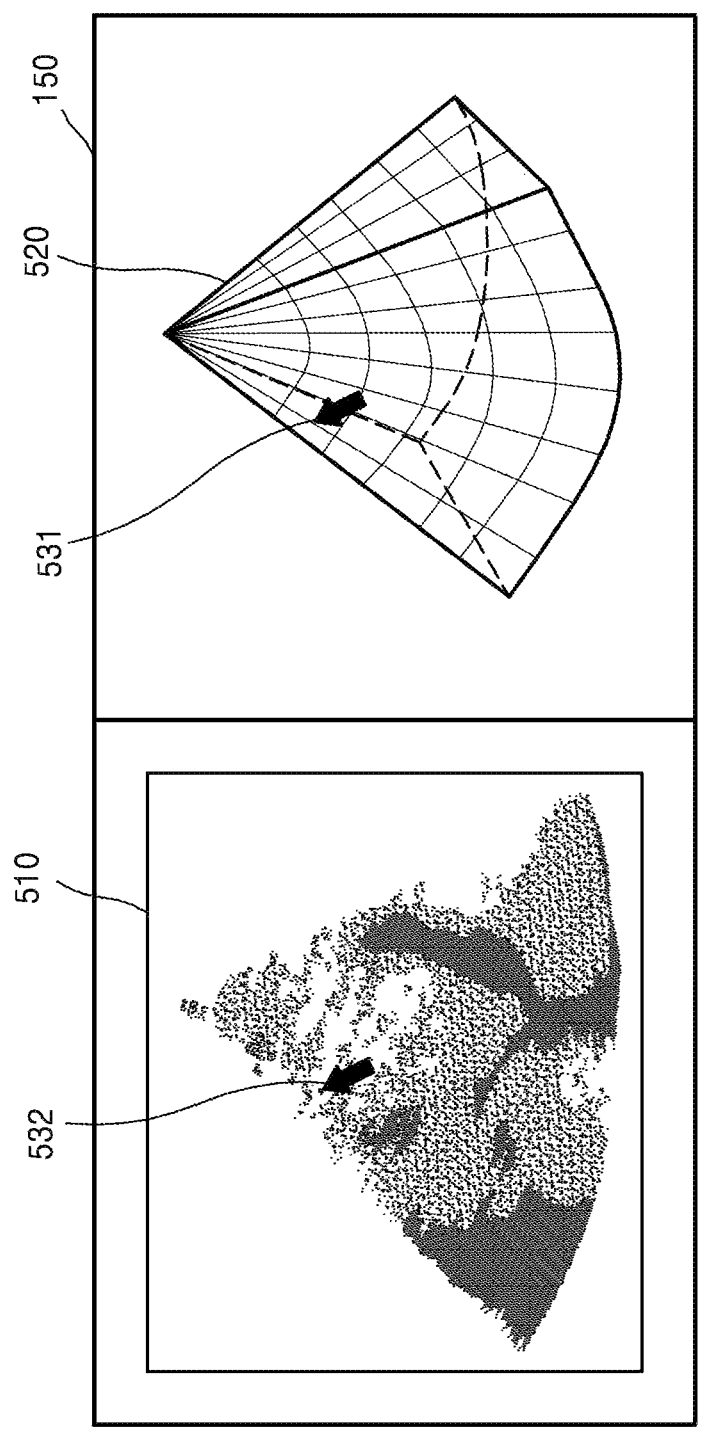
Figure 8:
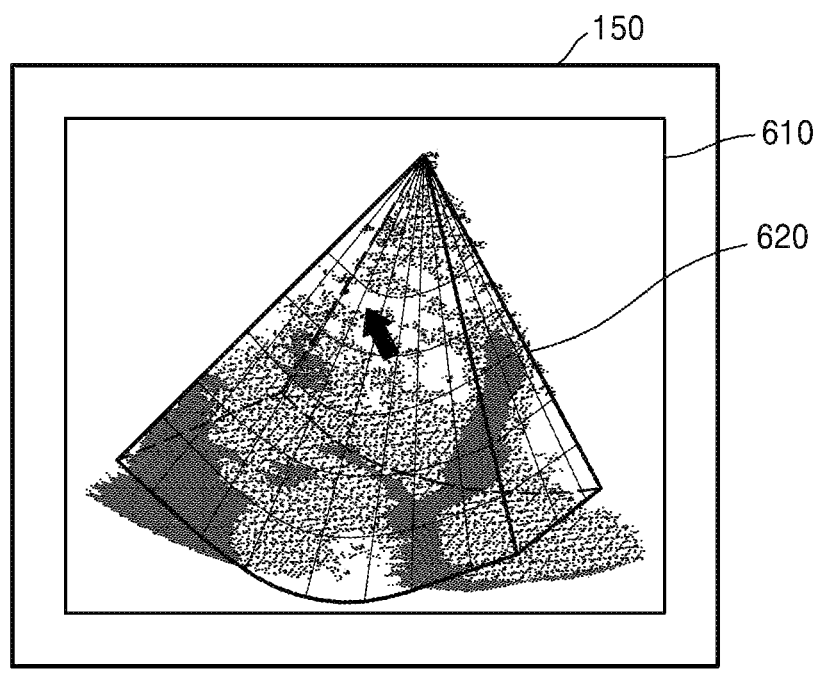

FIGS. 6 through 8 are diagrams for describing setting of a first voxel and a second voxel, according to exemplary embodiments.

Referring to FIG. 6, the volume rendering apparatus 100 may display a rendered image 410 obtained by performing volume rendering on volume data of an object, on a display unit 150. Here, the display unit 150 may correspond to the display unit 250 of FIG. 4.

The volume rendering apparatus 100 may receive a user input of selecting a certain region 420 included in the rendered image 410. For example, a user may select the certain region 420 included in the rendered image 410 by using an input tool, such as a touch tool, a mouse, a keyboard, a track ball, or a button. When the certain region 420 is selected, the volume rendering apparatus 100 may set voxels in the certain region 420 as first voxels, and the remaining voxels as second voxels.

Referring to FIG. 7, the volume rendering apparatus 100 may display a rendered image 510 obtained by rendering volume data of an object, and a modeling image 520 obtained by splitting the volume data into a plurality of regions, on the display unit 150. Here, the plurality of regions in the modeling image 520 may each include at least one voxel. In other words, one region may include one voxel, or one region may include at least two voxels.

The volume rendering apparatus 100 may receive an input of selecting at least one of a plurality of voxels included in the volume data, based on the modeling image 520. For example, a user may select at least one region included in the modeling image 520 by using an input tool, such as a touch tool, a mouse, a keyboard, a track ball, or a button.

Here, the volume rendering apparatus 100 may display a region corresponding to the region selected by the user, on the rendered image 510. For example, when the user moves a first arrow 531 displayed on the modeling image 520 by using a mouse, a second arrow 532 may be displayed on a certain region of the rendered image 510, which corresponds to a region of the modeling image 520 where the first arrow 531 is located. Also, when the region is selected, the volume rendering apparatus 100 may set voxels included in the region as first voxels, and the remaining voxels as second voxels.

Alternatively, the user may select a certain region included in the rendered image 510 by using an input tool, such as a touch tool, a mouse, or a keyboard. Here, the volume rendering apparatus 100 may display a region corresponding to the certain region on the modeling image 520. For example, when the user moves the second arrow 532 displayed on the rendered image 510 by using the mouse, the first arrow 531 may be displayed on a certain region of the modeling image 520, which corresponds to a region where the second arrow 532 is located. Also, when the certain region is selected, the volume rendering apparatus 100 may set voxels included in the certain region as first voxels, and the remaining voxels as second voxels.

Referring to FIG. 8, the volume rendering apparatus 100 may overlap and display a rendered image 610 and a modeling image 620, on the display unit 150. For example, a certain region of the rendered image 610 may overlap a certain region of the modeling image 620, which corresponds to the certain region of the rendered image 610. The volume rendering apparatus 100 may receive a user input of selecting a certain region included in an overlapped image. For example, a user may select a certain region included in the rendered image 610, by using an input tool, such as a touch tool, a mouse, or a keyboard. When the certain region is selected, the volume rendering apparatus 100 may set voxels in the certain region as first voxels, and the remaining voxels as second voxels.

In FIGS. 6 through 8, voxels in a selected region or selected voxels are set as first voxels and remaining voxels are set as second voxels, but an exemplary embodiment is not limited thereto, and at least one of the remaining voxels may be selected as a second voxel.

Also, since the volume rendering apparatus 100 according to an exemplary embodiment sets the first and second voxels based on user inputs, the volume rendering apparatus 100 may set some of voxels located at the same distance from a viewpoint of rendering as first voxels, and some of the remaining voxels as second voxels. Thus, different gain values or threshold values may be applied to the voxels located at the same distance from the viewpoint of the rendering.

FIGS. 9A through 11 are diagrams for describing setting of a first voxel and a second voxel, according to other exemplary embodiments.

Figure 9A:
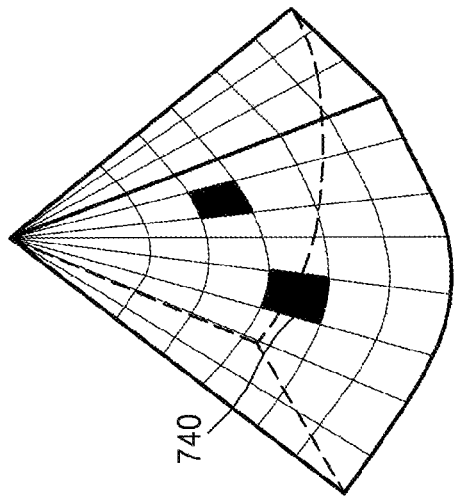
FIGS. 9A through 11 are diagrams for describing setting of a first voxel and a second voxel, according to other exemplary embodiments.
Figure 9B:
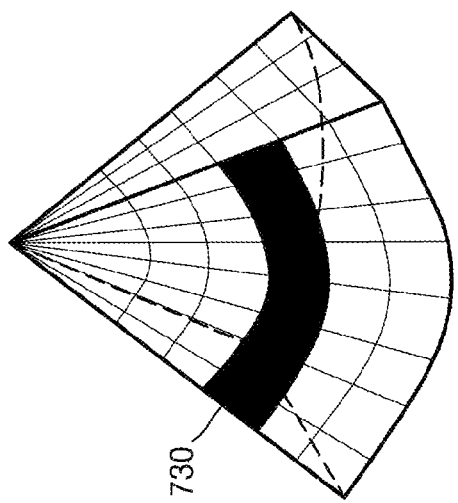
Figure 9C:
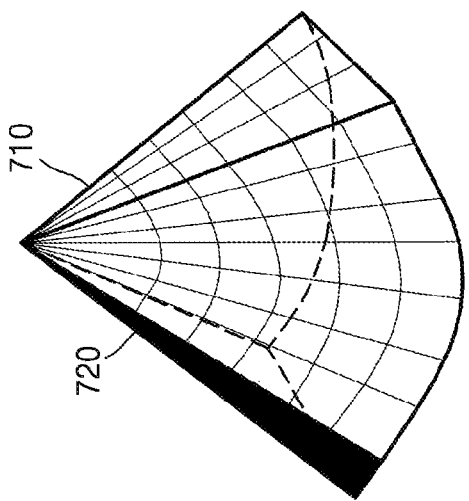

Referring to FIGS. 9A through 9C, a user may select at least one voxel included in volume data. For example, as shown in FIG. 9A, voxels 720 corresponding to one scan line may be selected, as shown in FIG. 9B, voxels 730 having the same depth may be selected, or as shown in FIG. 9C, voxels 740 at arbitrary locations may be selected, but an exemplary embodiment is not limited thereto.

Figure 10:
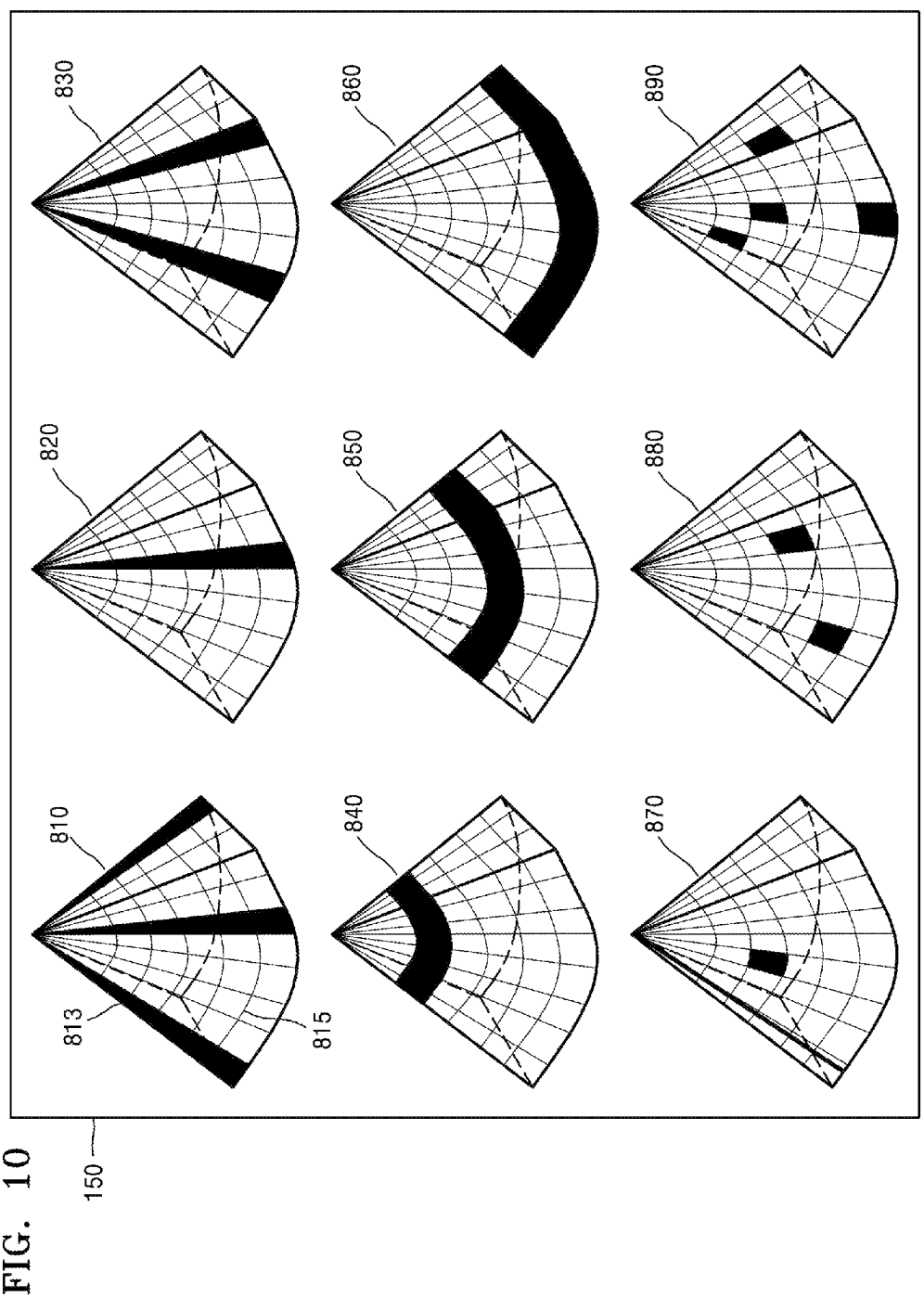

Referring to FIG. 10, the volume rendering apparatus 100 may display pre-set voxel selecting models 810 through 890 on the display unit 150, and select at least one voxel included in volume data by using the pre-set voxel selecting models 810 through 890.

The pre-set voxel selecting models 810 through 890 may be pre-set based on a shape of the volume data or a type of an object, or may be arbitrarily pre-set by a user.

For example, as shown in FIG. 10, the pre-set voxel selecting models 810 through 890 may include the pre-set voxel selecting models 810 through 830 that select voxels corresponding to a plurality of scan lines, the pre-set voxel selecting models 840 through 860 that select voxels corresponding to a plurality of depths, and the pre-set voxel selecting models 870 through 890 that select voxels at certain locations.

Also, at least one of the pre-set voxel selecting models 810 through 890 may be a model optimized according to the type of the object. For example, when the object is a heart, at least one of the pre-set voxel selecting models 810 through 890 may be a model of selecting voxels corresponding to a region in which an ultrasound signal is weak while scanning the heart.

Also, in the pre-set voxel selecting models 810 through 890, a voxel to be selected may be shaded.

As shown in FIG. 10, when the pre-set voxel selecting model 810 is selected from among the pre-set voxel selecting models 810 through 890 displayed on the display unit 150, the volume rendering apparatus 100 may set voxels (shaded voxels) corresponding to a first region 813 in the pre-set voxel selecting model 810 as first voxels, and voxels (not shaded voxels) corresponding to a second region 815 as second voxels. Alternatively, the volume rendering apparatus 100 may set the voxels corresponding to the first region 813 as second voxels, and the voxels corresponding to the second region 815 as first voxels. Alternatively, the volume rendering apparatus 100 may set the voxels corresponding to the first region 813 as first voxels, and select and set at least one of the voxels corresponding to the second region 815 as second voxels. However, an exemplary embodiment is not limited thereto.

Figure 11:
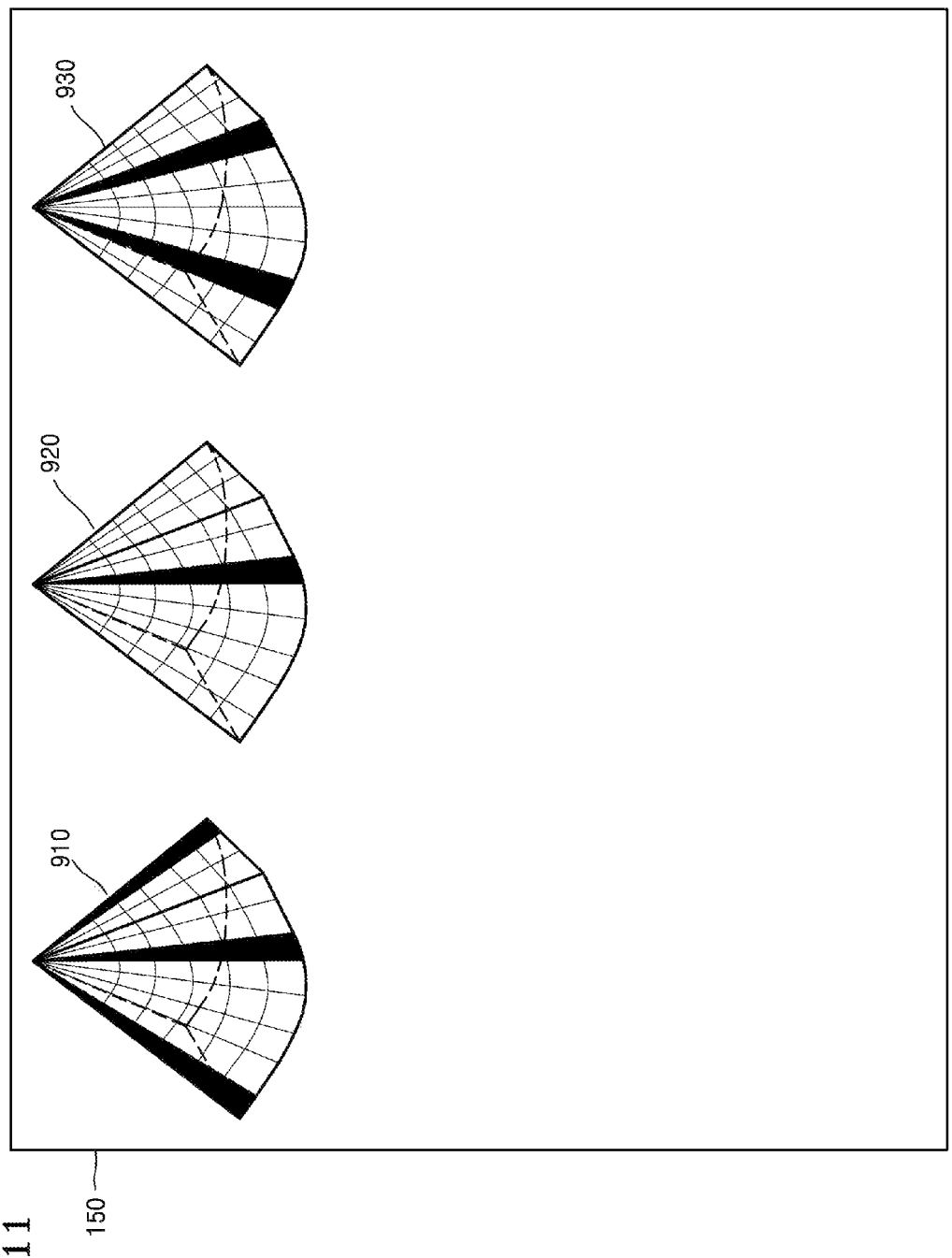

Referring to FIG. 11, the volume rendering apparatus 100 may display some of pre-stored voxel selecting models on the display unit 150.

When a user selects at least one of a plurality of voxels included in volume data, only some of voxel selecting models pre-stored in the volume rendering apparatus 100 may be displayed based on the selected voxel. For example, when the user selects a voxel at a first location, the volume rendering apparatus 100 may display a voxel selecting model of selecting the voxel at the first location from among a plurality of pre-set voxel selecting models.

Alternatively, when the user selects a type of an object, only some of voxel selecting models pre-stored in the volume rendering apparatus 100, which are related to the selected type of the object may be displayed.

As shown in FIG. 11, when voxel selecting models 910 through 930 are displayed, the user may select at least one of the voxel selecting models 910 through 930 to select voxels. Also, the volume rendering apparatus 100 may set first and second voxels based on the selected at least one of the voxel selecting models 910 through 930.

Figure 12:
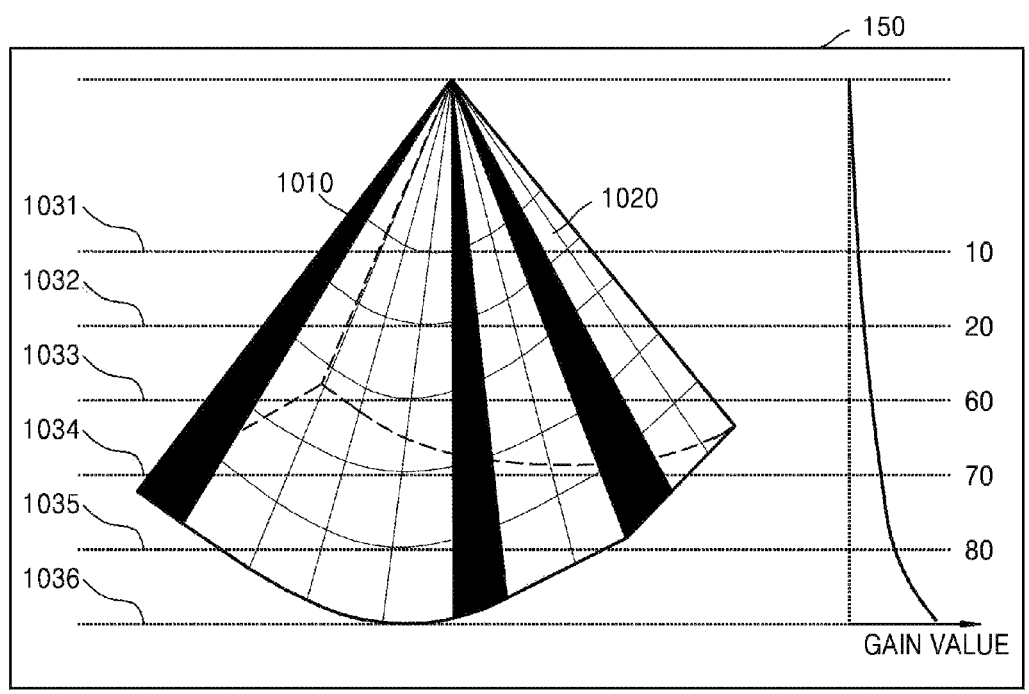
FIG. 12 is a reference diagram for describing a method of setting a gain value, according to an exemplary embodiment.

FIG. 12 is a reference diagram for describing a method of setting a gain value, according to an exemplary embodiment.

Referring to FIG. 12, the volume rendering apparatus 100 may set a gain value of at least one of first and second voxels. For convenience of description, shaded voxels are first voxels 1010 and not shaded voxels are second voxels 1020 in FIG. 12.

The volume rendering apparatus 100 according to an exemplary embodiment may set a gain value of the first voxel 1010 based on a user input. For example, as shown in FIG. 12, when the first voxels 1010 include voxels corresponding to a plurality of scan lines, i.e., first through third scan lines, the volume rendering apparatus 100 may set a gain value of the first voxels 1010 corresponding to each of the first through third scan lines.

For example, a user may select voxels corresponding to one of the first through third scan lines included in the first voxels 1010, and input gain values corresponding to reference depths of the selected voxels. As shown in FIG. 12, the user may input at least one of a gain value (for example, 10) corresponding to a first reference depth 1031, a gain value (for example, 20) corresponding to a second reference depth 1032, a gain value (for example, 60) corresponding to a third reference depth 1033, a gain value (for example, 70) corresponding to a fourth reference depth 1034, and a gain value (for example, 80) corresponding to a fifth reference depth 1035. Here, a brightness value of a voxel may increase when a gain value increases.

Also, the volume rendering apparatus 100 may obtain a continuous gain curve of a scan line based on input gain values, and set gain values at depths other than reference depths based on the gain curve.

Figure 13B:
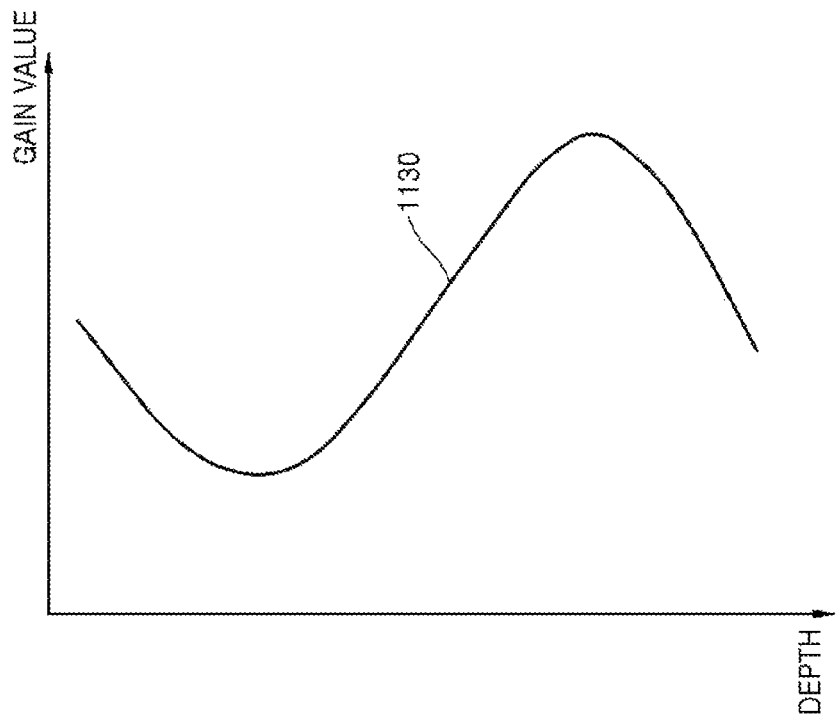
FIGS. 13A and 13B are diagrams of user interfaces for setting gain values corresponding to reference depths of one scan line, according to an exemplary embodiment.
Figure 13A:
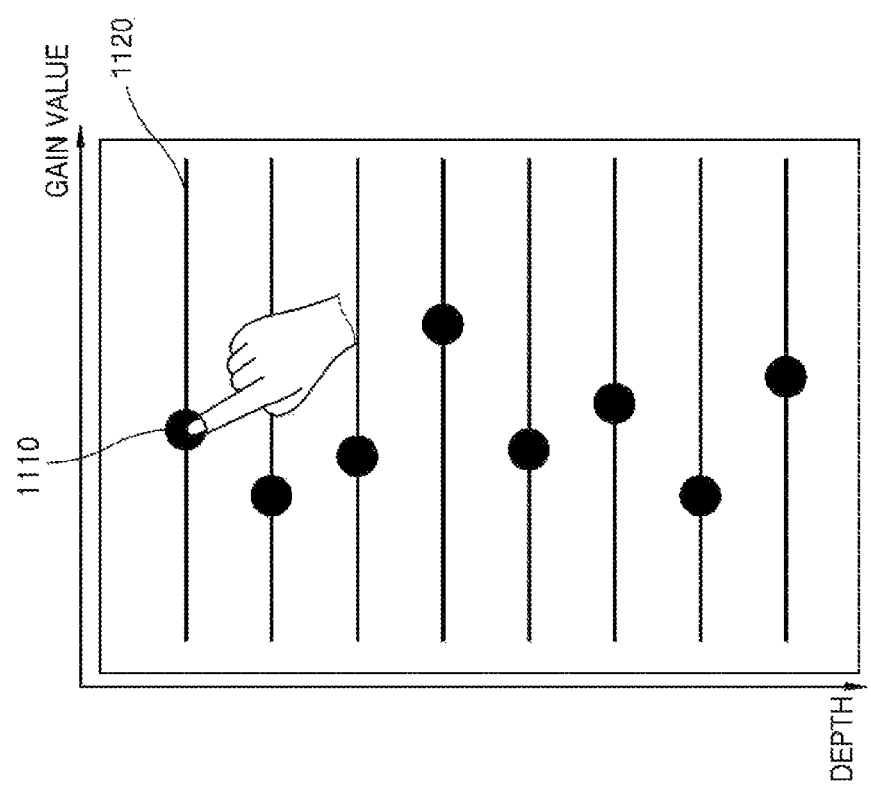

FIGS. 13A and 13B are diagrams of user interfaces for setting gain values corresponding to reference depths of one scan line, according to an exemplary embodiment.

Referring to FIG. 13A, the user interface may include a line 1120 corresponding to a reference depth, and a control bar 1110 for setting a gain value. A user may move the control bar 1110 on the line 1120 to set a gain value corresponding to each reference depth. For example, when the control bar 1110 moves to the right, the gain value increases, and thus a brightness value of a voxel may be further amplified.

Alternatively, the user may set the gain value corresponding to each reference depth by tapping a certain location on the line 1120. For example, when a tapping location is rightward, the gain value is set to be higher, and thus the brightness value of the voxel may be further amplified.

Also, the volume rendering apparatus 100 may obtain a continuous gain curve based on the gain values corresponding to the reference depths, and set gain values at depths other than the reference depths based on the gain curve.

Referring to FIG. 13B, a user may draw a gain curve 1130 for setting gain values by using an input tool. For example, the user may draw the gain curve 1130 on a touch screen by using a touch tool or a mouse, but an exemplary embodiment is not limited thereto.

Here, a horizontal axis denotes a gain value and a vertical axis denotes a depth. Also, the gain value increases from left to right on the horizontal axis and the depth increases from top to bottom on the vertical axis.

The volume rendering apparatus 100 may receive a gain curve input, and set gain values of voxels included in a scan line based on the gain curve input. In other words, a gain value at a first depth of a gain curve may be set as a gain value of a voxel at a first depth of a scan line.

Gain values of voxels corresponding to second and third scan lines may be set in the same manner described above with reference to FIGS. 12, 13A and 13B.

Also, the volume rendering apparatus 100 may set pre-set values as gain values of the second voxels 1020, or as described above with reference to FIGS. 12, 13A, and 13B, the gain values of the second voxels 1020 may be set based on user inputs.

Figure 14:
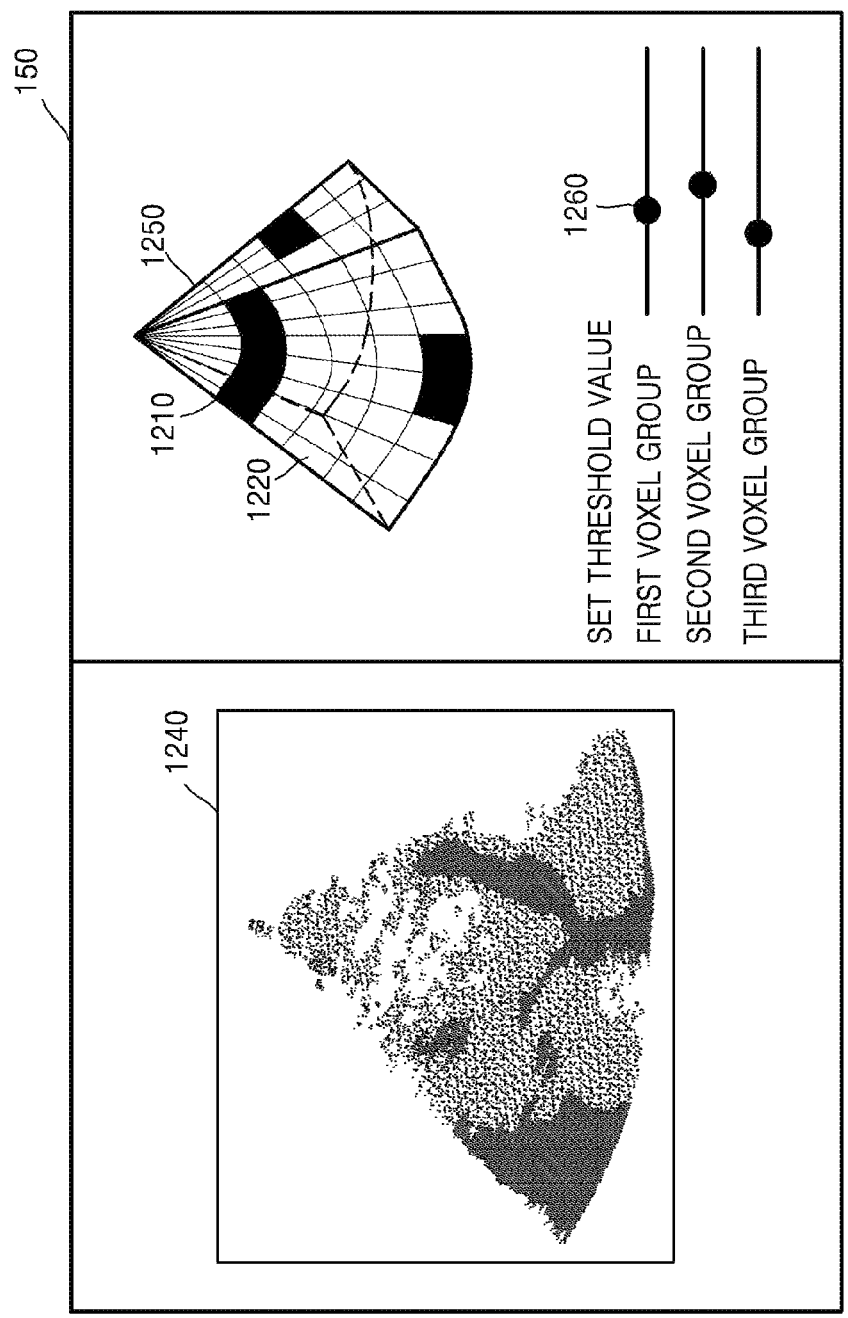
FIG. 14 is a reference diagram for describing a method of setting a threshold value, according to an exemplary embodiment.

FIG. 14 is a reference diagram for describing a method of setting a threshold value, according to an exemplary embodiment.

Referring to FIG. 14, the volume rendering apparatus 100 may set a threshold value of at least one of first and second voxels. For convenience of description, shaded voxels are first voxels 1210 and not shaded voxels are second voxels 1220 in FIG. 14.

The volume rendering apparatus 100 according to an exemplary embodiment may display an ultrasound image 1240 on a first region of the display unit 150, and a model image 1250 showing volume data on a second region of the display unit 150. Here, the model image 1250 includes a plurality of voxels, and the first and second voxels 1210 and 1220 may be distinguishably shown in the model image 1250.

The volume rendering apparatus 100 may set a threshold value of the first voxel 1210 based on a user input. For example, as shown in FIG. 14, when the first voxels 1210 include a plurality of voxel groups, i.e., first through third voxel groups, the volume rendering apparatus 100 may set a threshold value of voxels included in each of the first through third voxel groups.

For example, a user may set the threshold value of the first voxel group, the threshold value of the second voxel group, and the threshold value of the third voxel group by using a user interface shown in FIG. 14.

The user interface may include a plurality of control bars 1260 for setting the threshold value of each of the first through third voxel groups. The user may move the control bar 1260 on a line to set the threshold value of each of the first through third voxel groups. For example, the threshold value may increase when the control bar 1260 is located rightward.

Also, the volume rendering apparatus 100 may set a pre-set value as a threshold value of the second voxel 1220, or set the threshold value of the second voxel 1220 based on a user input.

The user interface shown in FIG. 14 is only an example, and the volume rendering apparatus 100 may provide any one of various user interfaces for setting a threshold value.

Figure 15:
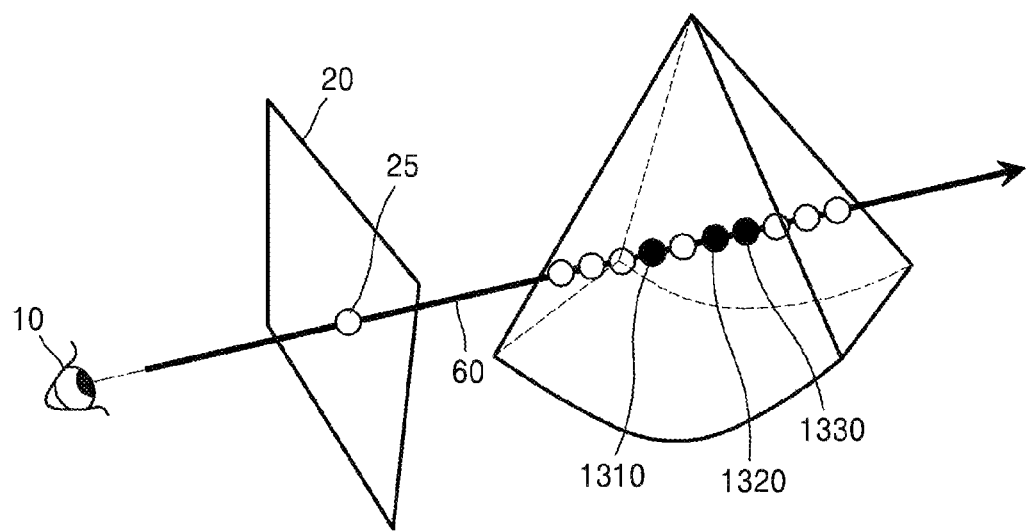
FIG. 15 is a reference diagram for describing a volume rendering method according to an exemplary embodiment.

FIG. 15 is a reference diagram for describing a volume rendering method according to an exemplary embodiment.

Referring to FIG. 15, the volume rendering apparatus 100 may emit the virtual ray 60 towards the certain pixel 25 from the viewpoint 10 in order to determine a value of the certain pixel 25 on the screen 20, and perform rendering by using voxels through which the virtual ray 60 penetrates from among voxels of volume data. At this time, the volume rendering apparatus 100 may apply a first gain value or a first threshold value to shaded voxels, i.e., first voxels 1310 through 1330, from among the voxels through which the virtual ray 60 penetrates, and apply a second gain value or a second threshold value to the remaining voxels that are not shaded, i.e., second voxels.

Since methods of setting first and second voxels have been described in detail above with reference to FIGS. 6 through 11, details thereof are not provided again. Also, since methods of setting a first gain value, a first threshold value, a second gain value, and a second threshold value have been described in detail above with reference to FIGS. 12 through 14, details thereof are not provided again.

The volume rendering apparatus 100 may apply a first gain value or a first threshold value to the first voxels 1310 through 1330. For example, the volume rendering apparatus 100 may perform volume rendering based on voxels that are equal to or higher than the first threshold value from among the first voxels 1310 through 1330. Alternatively, the volume rendering apparatus 100 may amplify or attenuate the first voxels 1310 through 1330 based on the first gain value, and perform the volume rendering on the amplified or attenuated first voxels 1310 through 1330.

Similarly, the volume rendering apparatus 100 may apply a second gain value or a second threshold value to the second voxels. For example, the volume rendering apparatus 100 may perform volume rendering based on voxels equal to or higher than the second threshold value from among the second voxels. Alternatively, the volume rendering apparatus 100 may amplify or attenuate the second voxels based on the second gain value, and perform the volume rendering on the amplified or attenuated second voxels.

Accordingly, when the volume rendering apparatus 100 performs rendering on volume data of an object, the rendering may be performed by applying a first threshold value or a first gain value to voxels set to be first voxels from among voxels included in the volume data, and applying a second threshold value or a second gain value to voxels set to be second voxels.

As such, the volume rendering apparatus 100 performs the rendering by applying different threshold values or different gain values to the voxels included in the volume data, and thus may obtain a 3D image having the improved image quality.

FIGS. 16A and 16B are diagrams of volume rendered images according to exemplary embodiments.

FIG. 16A illustrates a rendered image on which volume rendering is performed by applying the same threshold value or the same gain value to voxels included in volume data of a heart.

In FIG. 16A, when the same threshold value is applied to the volume data, values of voxel in first through third regions 1410 through 1430 of the rendered image are set to be 0 due to a weak ultrasound signal, and thus the voxels are not shown in the rendered image.

FIG. 16B illustrates a rendered image on which volume rendering is performed by applying a threshold value or a gain value to the voxels in the first through third regions 1410 through 1430 of FIG. 16A, which is different from that of voxels in other regions.

In FIG. 16B, the image quality of the other regions is maintained to be equal to that of the rendered image of FIG. 16A, while the image quality of the first through third regions 1410 through 1430 is improved compared to that of the rendered image of FIG. 16A.

Figure 17A:
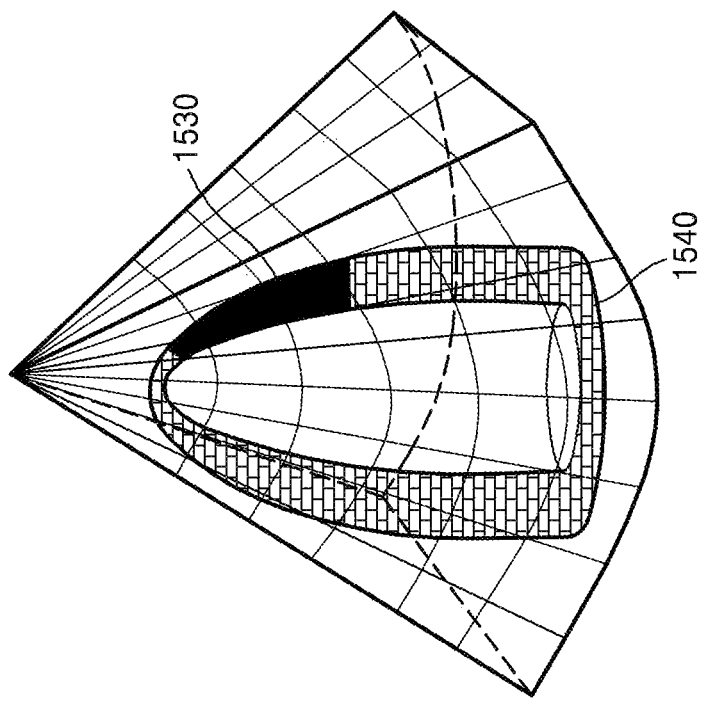
FIGS. 17A and 17B are reference diagrams for describing a volume rendering method according to an exemplary embodiment.
Figure 17B:
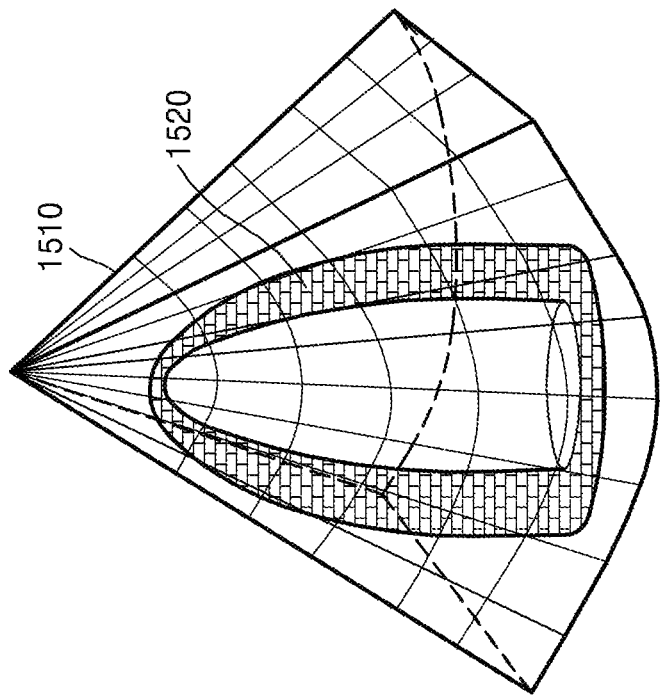

FIGS. 17A and 17B are reference diagrams for describing a volume rendering method according to an exemplary embodiment.

The volume rendering apparatus 100 may perform volume rendering by applying a gain value or a threshold value to volume data by using a voxel selecting model pre-set based on a type of an object.

The volume rendering apparatus 100 may analyze a plurality of ultrasound data samples according to objects, and set a gain value or a threshold value of voxels included in volume data. For example, a gain value of a voxel at a location where an ultrasound signal is weak may be set to be higher than that of another voxel.

A voxel selecting model may be set such that a region where an ultrasound signal is weak or a region having a value of an ultrasound signal, which is within a pre-set range, is selected based on a type of an object. Here, the region where an ultrasound signal is weak or the region having a value of an ultrasound signal, which is within a pre-set range, may be determined by analyzing a plurality of ultrasound data samples according to objects.

For example, when volume data is about a heart, the volume rendering apparatus 100 may set a gain value or a threshold value of a voxel included in the volume data by using a voxel selecting model 1510 of a heart, as shown in FIG. 17A.

At this time, the voxel selecting model 1510 may be set such that voxels corresponding to a first region 1520 are selected. The first region 1520 may be a region where the voxels have similar brightness values, and thus the volume rendering apparatus 100 may set a gain value such that the brightness values of the voxels corresponding to the first region 1520 have similar values.

For example, as shown in FIG. 17B, when brightness values of voxels corresponding to a second region 1530 that is a part of the first region 1520 are not similar to those corresponding to the remaining region 1540 of the first region 1520, gain values applied to the voxels corresponding to the second region 1530 may be set based on the brightness values of the voxels corresponding to the remaining region 1540. Alternatively, gain values applied to the voxels corresponding to the remaining region 1540 may be set based on the brightness values of the voxels corresponding to the second region 1530.

Figure 18:
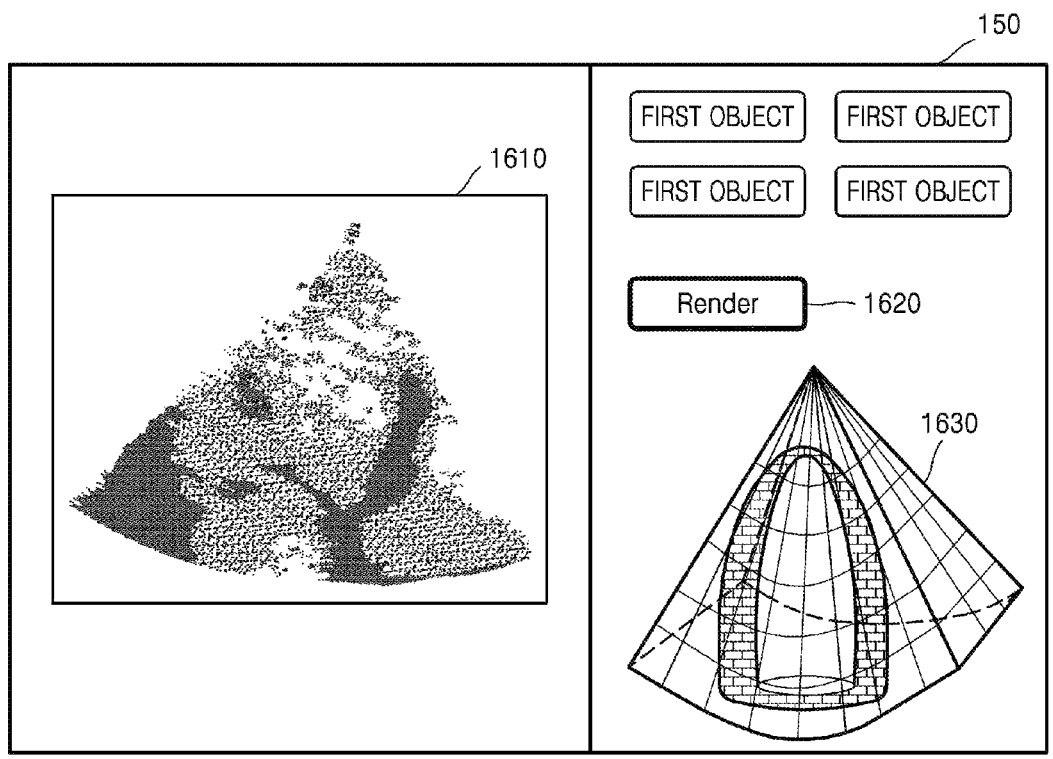
FIG. 18 is a diagram of a display unit of a volume rendering apparatus, according to an exemplary embodiment.

FIG. 18 is a diagram of the display unit 150 of the volume rendering apparatus 100, according to an exemplary embodiment.

Referring to FIG. 18, the volume rendering apparatus 100 according to an exemplary embodiment may display a rendered image 1610 obtained by performing volume rendering on volume data of an object, on a first region of the display unit 150. Also, the volume rendering apparatus 100 may display a menu for selecting a type of an object, on a second region of the display unit 150.

Upon receiving an input of selecting the object and an input of selecting a rendering button 1620 from a user, the volume rendering apparatus 100 may perform rendering by applying a voxel selecting model 1630 and a parameter (for example, a gain value or a threshold value), which are pre-set with respect to the selected object, to the volume data. At this time, the volume rendering apparatus 100 may display the voxel selecting model 1630 applied during the rendering on the display unit 150.

Alternatively, the volume rendering apparatus 100 may not receive an input of selecting an object from the user, but may automatically analyze a type of the object based on characteristics of the volume data. Then, the volume rendering apparatus 100 may perform the rendering by applying a voxel selecting mode and a parameter (for example, a gain value or a threshold value), which are pre-set with respect to the analyzed object, to the volume data.

As described above, according to one or more exemplary embodiments, a quality of a rendered image may be improved overall by setting a gain value or a threshold value of some of voxels included in volume data.

One or more exemplary embodiments may also be embodied as computer-readable codes on a computer-readable recording medium. The computer-readable recording medium is any data storage device that may store data which may be thereafter read by a computer system. Examples of the computer-readable recording medium include read-only memory (ROM), random-access memory (RAM), CD-ROMs, magnetic tapes, floppy disks, optical data storage devices, etc. The computer-readable recording medium can also be distributed over network coupled computer systems so that the computer-readable code is stored and executed in a distributed fashion.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. A volume rendering method for an ultrasound diagnosis apparatus including a probe, the volume rendering method comprising:
   obtaining three-dimensional (3D) ultrasound volume data of an object;
   receiving a user input of selecting a pre-set voxel selecting model;
   displaying the pre-set voxel selecting model corresponding to the object, wherein a shape of the pre-set voxel selecting model corresponds to a type of the probe;
   determining a first voxel and a second voxel by applying the pre-set voxel selecting model to the 3D ultrasound volume data;
   determining a first gain value of the first voxel included in the 3D ultrasound volume data based on a type of the object and a location of the first voxel, and a second gain value of the second voxel included in the 3D ultrasound volume data based on the type of the object and a location of the second voxel; and
   performing rendering by applying the first gain value to the first voxel and the second gain value to the second voxel,
   wherein the pre-set voxel selecting model is set such that a region, in which a brightness value of a voxel included in the 3D ultrasound volume is lower than a preset value or is within a preset range, is selected as one among the first voxel and the second voxel.

2. The volume rendering method of claim 1, further comprising:
setting a first threshold value of the first voxel included in the 3D ultrasound volume data, and a second threshold value of the second voxel included in the 3D ultrasound volume data,
wherein the performing the rendering comprises performing the rendering by applying the first threshold value to the first voxel and the second threshold value to the second voxel.

3. The volume rendering method of claim 1, wherein the performing of the rendering comprises amplifying or attenuating a brightness value of the first voxel based on the first gain value, and amplifying or attenuating a brightness value of the second voxel based on the second gain value.

4. The volume rendering method of claim 2, wherein the performing of the rendering comprises setting a brightness value of the first voxel to 0 when the brightness value of the first voxel is lower than the first threshold value, and setting a brightness value of the second voxel to 0 when the brightness value of the second voxel is lower than the second threshold value.

5. The volume rendering method of claim 1, wherein the first voxel and the second voxel are voxels located at a same distance from a viewpoint of the rendering.

6. The volume rendering method of claim 1, further comprising receiving a user input of setting at least one among the first gain value and the second gain value.

7. A non-transitory computer-readable recording medium having recorded thereon a program, which when executed by a computer, performs the volume rendering method of claim 1.

8. A volume rendering apparatus for an ultrasound image, the volume rendering apparatus comprising:
an image processor that receives three dimensional (3D) ultrasound volume data of an object, receives a user input of selecting a pre-set voxel selecting model, displays the pre-set voxel selecting model corresponding to the object, wherein a shape of the pre-set voxel selecting model corresponds to a type of a probe, determines a first voxel and a second voxel by applying the pre-set voxel selecting model to the 3D ultrasound volume data, determines a first gain value of the first voxel included in the 3D ultrasound volume data based on a type of the object and a location of the first voxel, determines a second gain value of the second voxel included in the 3D ultrasound volume data based on the type of the object and a location of the second voxel, and performs rendering by applying the first gain value to the first voxel and the second gain value to the second voxel; and
a display configured to display the ultrasound image rendered,
wherein the pre-set voxel selecting model is set such that a region, in which a brightness value of a voxel included in the 3D ultrasound volume is lower than a preset value or is within a preset range, is selected as one among the first voxel and the second voxel.

9. The volume rendering apparatus of claim 8, wherein the image processor sets a first threshold value of the first voxel included in the 3D ultrasound volume data, and a second threshold value of the second voxel included in the 3D ultrasound volume data, and
performs the rendering by applying the first threshold value to the first voxel and the second threshold value to the second voxel.

10. The volume rendering apparatus of claim 8, wherein the image processor amplifies or attenuates a brightness value of the first voxel based on the first gain value, and amplifies or attenuates a brightness value of the second voxel based on the second gain value.

11. The volume rendering apparatus of claim 9, wherein the image processor sets a brightness value of the first voxel to 0 when the brightness value of the first voxel is lower than the first threshold value, and sets a brightness value of the second voxel to 0 when the brightness value of the second voxel is lower than the second threshold value.

12. The volume rendering apparatus of claim 8, wherein the first voxel and the second voxel are voxels located at a same distance from a viewpoint of the rendering.

13. The volume rendering apparatus of claim 8, further comprising a user interface that receives a user input of setting at least one among the first gain value and the second gain value.

* * * * *